United States Patent
Bass et al.

(10) Patent No.: US 8,945,003 B2
(45) Date of Patent: Feb. 3, 2015

(54) SURGICAL RETRACTOR WITH CURVED ROTATING BLADES

(75) Inventors: Daniel Bass, El Granada, CA (US); Ray Bertolero, Danville, CA (US); Terry Johnston, Redwood City, CA (US); Danny Fishman, Houston, TX (US)

(73) Assignee: Tedan Surgical, Houston, TX (US)

( * ) Notice: Subject to any disclaimer, the term of this patent is extended or adjusted under 35 U.S.C. 154(b) by 419 days.

(21) Appl. No.: 13/005,363

(22) Filed: Jan. 12, 2011

(65) Prior Publication Data
US 2011/0172494 A1     Jul. 14, 2011

Related U.S. Application Data

(60) Provisional application No. 61/294,362, filed on Jan. 12, 2010.

(51) Int. Cl.
*A61B 1/32*      (2006.01)
*A61B 17/02*     (2006.01)
*A61B 19/00*     (2006.01)

(52) U.S. Cl.
CPC .............. *A61B 17/0206* (2013.01); *A61B 17/02* (2013.01); *A61B 19/5202* (2013.01)
USPC ............................ 600/215; 600/214; 600/219

(58) Field of Classification Search
CPC .................................................. A61B 17/0206
USPC .................................................. 600/201–217
See application file for complete search history.

(56) References Cited

U.S. PATENT DOCUMENTS

| | | | |
|---|---|---|---|
| 3,729,006 A | 4/1973 | Wilder et al. | |
| 4,562,832 A | 1/1986 | Wilder et al. | |
| 4,627,421 A * | 12/1986 | Symbas et al. | 600/232 |
| 4,747,395 A | 5/1988 | Brief | |
| 4,754,746 A | 7/1988 | Cox | |
| 4,807,600 A * | 2/1989 | Hayes | 600/203 |
| 4,889,107 A | 12/1989 | Kaufman | |

(Continued)

FOREIGN PATENT DOCUMENTS

GB     2218912 A     11/1989

OTHER PUBLICATIONS

International Search Report for PCT/US2011/020976 dated Sep. 5, 2011.

(Continued)

*Primary Examiner* — Eduardo C Robert
*Assistant Examiner* — Stuart S Bray
(74) *Attorney, Agent, or Firm* — Kramer Amado P.C.

(57) ABSTRACT

Various embodiments of the present invention provide a surgical retractor having two blade-supporting arms, which are mounted to be laterally slideable towards and apart from each other by a toothed rack. Each arm supports a respective retractor blade. In some embodiments, the retractor blades are curved in the same direction as each other so that the first blade is concave in the first direction, and a second blade is also concave in the same direction. Alternatively or additionally, in some embodiments, a cushioned material or cushioned sleeve is present on the blades where the blades contact the anatomy. The cushioned material or sleeve may be made of a soft silicone. Further, the cushioned material or sleeve may be coated or molded onto the blade structure, or may be a removable sleeve that is manually slid onto or off of the blade structure. Also, alternatively or in addition in some embodiments, blade-mounted lighting may be provided.

19 Claims, 7 Drawing Sheets

(56) References Cited

U.S. PATENT DOCUMENTS

| | | | |
|---|---|---|---|
| 5,007,409 A | 4/1991 | Pope | |
| 5,512,038 A * | 4/1996 | O'Neal et al. | 600/210 |
| 5,707,281 A * | 1/1998 | Hicks | 452/197 |
| 5,928,139 A * | 7/1999 | Koros et al. | 600/205 |
| 5,931,777 A | 8/1999 | Sava | |
| 5,944,736 A * | 8/1999 | Taylor et al. | 606/198 |
| 5,967,972 A * | 10/1999 | Santilli et al. | 600/232 |
| 5,984,867 A * | 11/1999 | Deckman et al. | 600/232 |
| 6,074,343 A * | 6/2000 | Nathanson et al. | 600/214 |
| 6,132,370 A * | 10/2000 | Furnish et al. | 600/235 |
| 6,228,025 B1 * | 5/2001 | Hipps et al. | 600/213 |
| 6,309,349 B1 | 10/2001 | Bertolero et al. | |
| 6,338,712 B2 * | 1/2002 | Spence et al. | 600/201 |
| 6,340,345 B1 | 1/2002 | Lees et al. | |
| 6,468,207 B1 | 10/2002 | Fowler, Jr. | |
| 6,482,153 B1 | 11/2002 | Hipps et al. | |
| 6,500,116 B1 * | 12/2002 | Knapp | 600/232 |
| 6,837,851 B1 * | 1/2005 | Valentini et al. | 600/210 |
| 6,974,412 B2 | 12/2005 | Dobrovolny | |
| 7,182,729 B2 | 2/2007 | Abdelgany et al. | |
| 7,294,103 B2 | 11/2007 | Bertolero et al. | |
| 7,537,565 B2 * | 5/2009 | Bass | 600/219 |
| 7,582,058 B1 | 9/2009 | Miles et al. | |
| 7,588,537 B2 * | 9/2009 | Bass | 600/234 |
| 7,686,492 B2 * | 3/2010 | Vayser et al. | 362/572 |
| 7,691,057 B2 * | 4/2010 | Miles et al. | 600/219 |
| 7,775,974 B2 * | 8/2010 | Buckner et al. | 600/202 |
| 7,819,801 B2 * | 10/2010 | Miles et al. | 600/224 |
| 7,892,173 B2 * | 2/2011 | Miles et al. | 600/210 |
| 7,909,761 B2 * | 3/2011 | Banchieri et al. | 600/208 |
| 7,922,658 B2 * | 4/2011 | Cohen et al. | 600/223 |
| 7,935,051 B2 * | 5/2011 | Miles et al. | 600/202 |
| 7,951,077 B2 * | 5/2011 | Sayeg et al. | 600/210 |
| 7,981,158 B2 * | 7/2011 | Fitz et al. | 623/17.16 |
| 7,988,625 B2 * | 8/2011 | Abdelgany et al. | 600/220 |
| 8,047,987 B2 * | 11/2011 | Grey et al. | 600/245 |
| 8,088,066 B2 * | 1/2012 | Grey et al. | 600/212 |
| 8,092,378 B2 * | 1/2012 | Roth et al. | 600/206 |
| 8,114,016 B2 * | 2/2012 | Lo et al. | 600/202 |
| 8,132,949 B2 * | 3/2012 | Vayser et al. | 362/572 |
| 8,133,173 B2 * | 3/2012 | Miles et al. | 600/202 |
| 8,172,750 B2 * | 5/2012 | Miles et al. | 600/202 |
| 8,182,423 B2 * | 5/2012 | Miles et al. | 600/214 |
| 8,187,179 B2 * | 5/2012 | Miles et al. | 600/210 |
| 8,192,357 B2 * | 6/2012 | Miles et al. | 600/202 |
| 8,246,538 B2 * | 8/2012 | Gorek | 600/206 |
| 8,376,937 B2 * | 2/2013 | Xia et al. | 600/202 |
| 8,376,940 B2 * | 2/2013 | Gorek | 600/206 |
| 8,409,088 B2 * | 4/2013 | Grey et al. | 600/212 |
| 8,435,174 B2 * | 5/2013 | Cropper et al. | 600/203 |
| 8,444,557 B2 * | 5/2013 | Schleitweiler et al. | 600/210 |
| 8,454,503 B2 * | 6/2013 | Roth et al. | 600/206 |
| 8,480,704 B2 * | 7/2013 | Heiges et al. | 606/207 |
| 8,529,444 B2 * | 9/2013 | Hale | 600/206 |
| 2001/0041827 A1 * | 11/2001 | Spence et al. | 600/201 |
| 2001/0041828 A1 * | 11/2001 | Deckman et al. | 600/232 |
| 2002/0055670 A1 * | 5/2002 | Weiss | 600/220 |
| 2003/0149341 A1 | 8/2003 | Clifton | |
| 2005/0080320 A1 * | 4/2005 | Lee et al. | 600/214 |
| 2005/0267336 A1 * | 12/2005 | Bertolero et al. | 600/219 |
| 2006/0084844 A1 * | 4/2006 | Nehls | 600/227 |
| 2006/0224044 A1 | 10/2006 | Marchek et al. | |
| 2007/0073111 A1 | 3/2007 | Bass | |
| 2007/0083086 A1 * | 4/2007 | LeVahn et al. | 600/210 |
| 2007/0225571 A1 | 9/2007 | Branch et al. | |
| 2007/0293729 A1 * | 12/2007 | Grey et al. | 600/212 |
| 2008/0021285 A1 * | 1/2008 | Drzyzga et al. | 600/215 |
| 2008/0058606 A1 * | 3/2008 | Miles et al. | 600/214 |
| 2008/0188718 A1 * | 8/2008 | Spitler et al. | 600/213 |
| 2008/0262494 A1 * | 10/2008 | Moore et al. | 606/53 |
| 2009/0112068 A1 * | 4/2009 | Grey et al. | 600/212 |
| 2009/0203969 A1 * | 8/2009 | Cohen et al. | 600/245 |
| 2009/0227845 A1 * | 9/2009 | Lo et al. | 600/212 |
| 2009/0259107 A1 * | 10/2009 | Crenshaw et al. | 600/202 |
| 2009/0259108 A1 * | 10/2009 | Miles et al. | 600/202 |
| 2010/0022845 A1 * | 1/2010 | Ott et al. | 600/215 |
| 2010/0041955 A1 * | 2/2010 | Grey et al. | 600/212 |
| 2010/0081885 A1 * | 4/2010 | Wing et al. | 600/215 |
| 2010/0094093 A1 * | 4/2010 | Miles et al. | 600/202 |
| 2010/0137690 A1 * | 6/2010 | Miles et al. | 600/202 |
| 2010/0152603 A1 * | 6/2010 | Miles et al. | 600/546 |
| 2010/0160738 A1 * | 6/2010 | Miles et al. | 600/202 |
| 2010/0174146 A1 * | 7/2010 | Miles et al. | 600/202 |
| 2010/0174147 A1 * | 7/2010 | Miles et al. | 600/202 |
| 2010/0174148 A1 * | 7/2010 | Miles et al. | 600/202 |
| 2011/0087074 A1 * | 4/2011 | Hardenbrook | 600/210 |
| 2011/0144439 A1 * | 6/2011 | Miles et al. | 600/202 |
| 2011/0196209 A1 * | 8/2011 | Shipp | 600/215 |
| 2012/0130180 A1 * | 5/2012 | Pell et al. | 600/206 |
| 2012/0203070 A1 * | 8/2012 | Crenshaw et al. | 600/202 |
| 2012/0316401 A1 * | 12/2012 | Matsumura | 600/235 |
| 2013/0237766 A1 * | 9/2013 | Pell et al. | 600/211 |

OTHER PUBLICATIONS

Extended International Search Report for PCT/US 2011/020976; dated Sep. 3, 2013.

JP Office Action dated Jul. 22, 2014 for JP Application No. 2012-5409026.

* cited by examiner

SURGICAL RETRACTOR WITH CURVED ROTATING BLADES

This application claims the benefit of U.S. Provisional Application No. 61/294,362, filed on Jan. 12, 2010 and the entire disclosures of which is incorporated herein by reference.

TECHNICAL FIELD

Some embodiments of the invention relate to surgical devices and methods, and particularly surgical retractors.

BACKGROUND

Surgical procedures often require the creation of a surgical exposure to allow a surgeon to reach deeper regions of the body. The surgical exposure is usually started with an incision of a suitable depth. Surgical instruments known as retractors are then inserted into the incision and used to spread skin, ribs and other soft tissue and bone structures and to pull back skin, muscle and other soft tissue to permit access to the desired area. Several handheld surgical retractors are known. In the case of cardiovascular/thoracic surgeries, it is desirable to reduce pressure points on the nerve and on the ribs.

SUMMARY

Various embodiments of the present invention provide a surgical retractor having two blade-supporting arms, which are mounted to be laterally slideable towards and apart from each other by a toothed rack. Each arm supports a respective retractor blade. In some embodiments, the retractor blades are curved in the same direction as each other, so that the first blade is concave in the first direction, and a second blade is also concave in the same direction. Alternatively or additionally, in some embodiments, a cushioned material or cushioned sleeve is present on the blades where the blades contact the anatomy. The cushioned material or sleeve may be made of a soft silicone. Further, the cushioned material or sleeve may be coated or molded onto the blade structure, or may be a removable sleeve that is manually slid onto or off of the blade structure. Also, alternatively or in addition in sonic embodiments, blade-mounted lighting may be provided. In some embodiments, the lighting may comprise a fiber optic light source that penetrates into and through the blade and terminates in an opening in the blade facing inward so that it shines light inwardly towards the direction of the other blade and/or towards the anatomy. One or both of the two opposed blades may have light sources shining generally inward. In some aspects of some embodiments there is provided a surgical retractor having a pair of arms mounted to be laterally slideable towards and apart from each other; and a respective first and second retractor blade, each supported on a respective arm and curved in the same direction as the other blade. In some aspects of some embodiments there is provided a surgical retractor having a first arm; a first retractor blade connected to the first arm, the first retractor blade having a first inner surface with a convex shape; a second arm; and a second retractor blade connected to the second arm, the second retractor blade having a second inner surface with a concave shape, wherein the first and second arms are mounted to be laterally slideable towards and apart from each other, and so that the first inner surface and the second inner surface face towards each other. In some aspects of some embodiments there is provided a surgical retractor having a first retractor blade connected to the first arm, the first retractor blade having a first inner surface with a convex shape; a second retractor blade connected to the second arm, the second retractor blade having a second inner surface with a concave shape; and a mount to which the first and second retractor blades are mounted to be laterally slideable towards and apart from each other, and so that the first inner surface and the second inner surface face towards each other .

The foregoing objects and advantages of the invention are illustrative of those that can be achieved by the various exemplary embodiments and are not intended to be exhaustive or limiting of the possible advantages which can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

BRIEF DESCRIPTION OF THE DRAWINGS

Examples of the invention are illustrated, without limitation, in the accompanying figures in which like numeral references refer to like elements.

DETAILED DESCRIPTION

Figure 1:
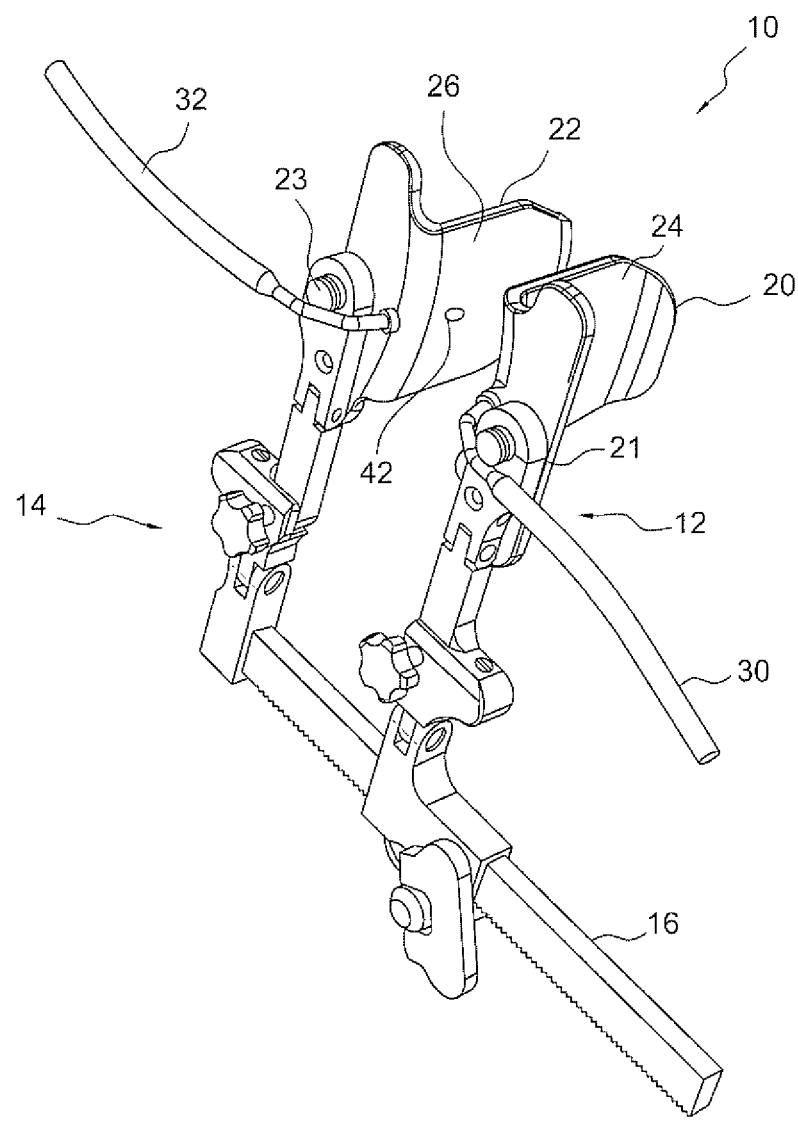
FIG. 1 is a perspective view of a surgical retractor according to a preferred embodiment of the invention.
Figure 2:
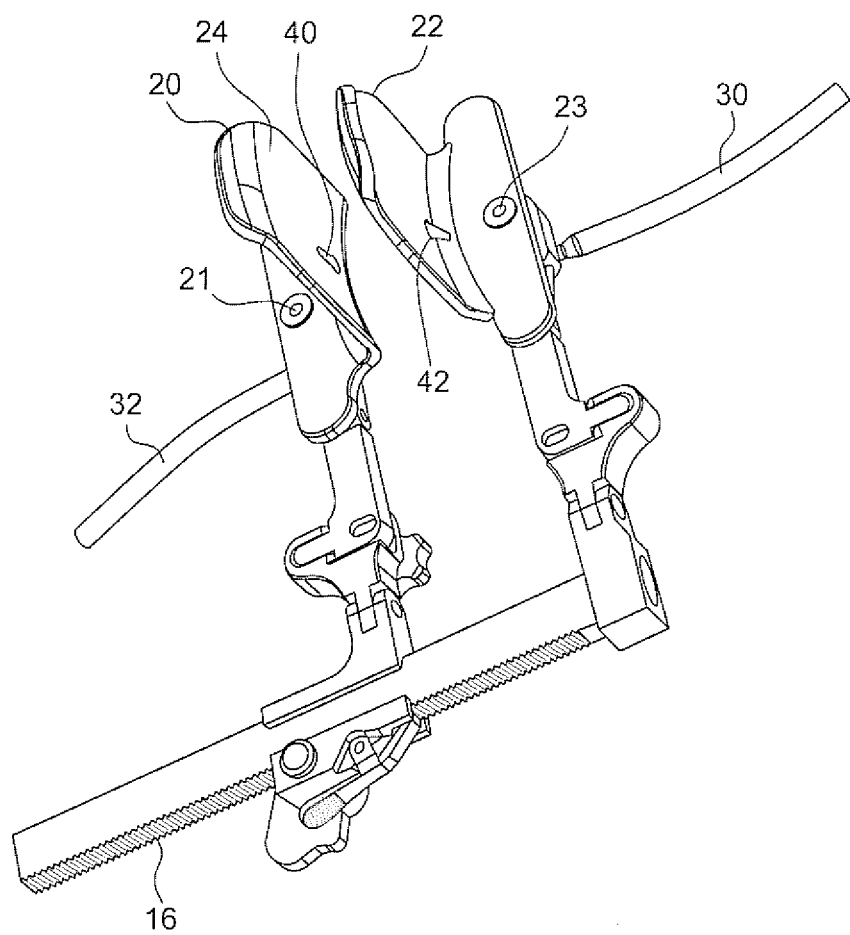
FIG. 2 is a perspective view of the surgical retractor taken from a different angle.
Figure 3:
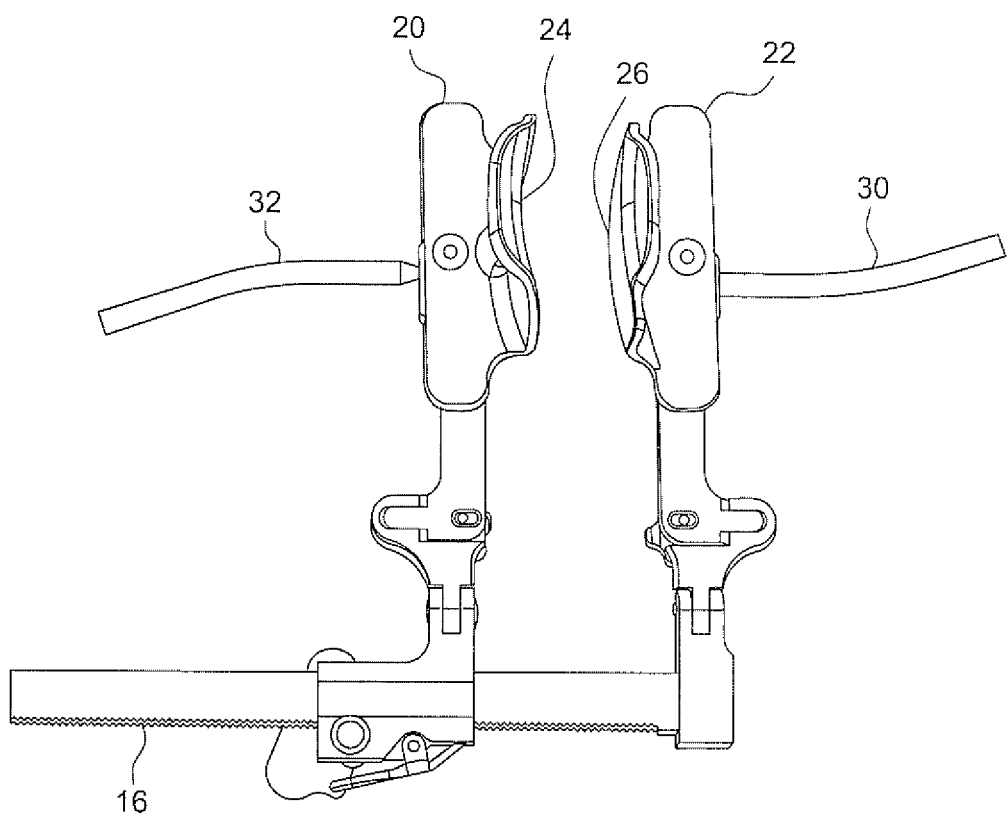
FIG. 3 is a front view of the surgical retractor.
Figure 4:
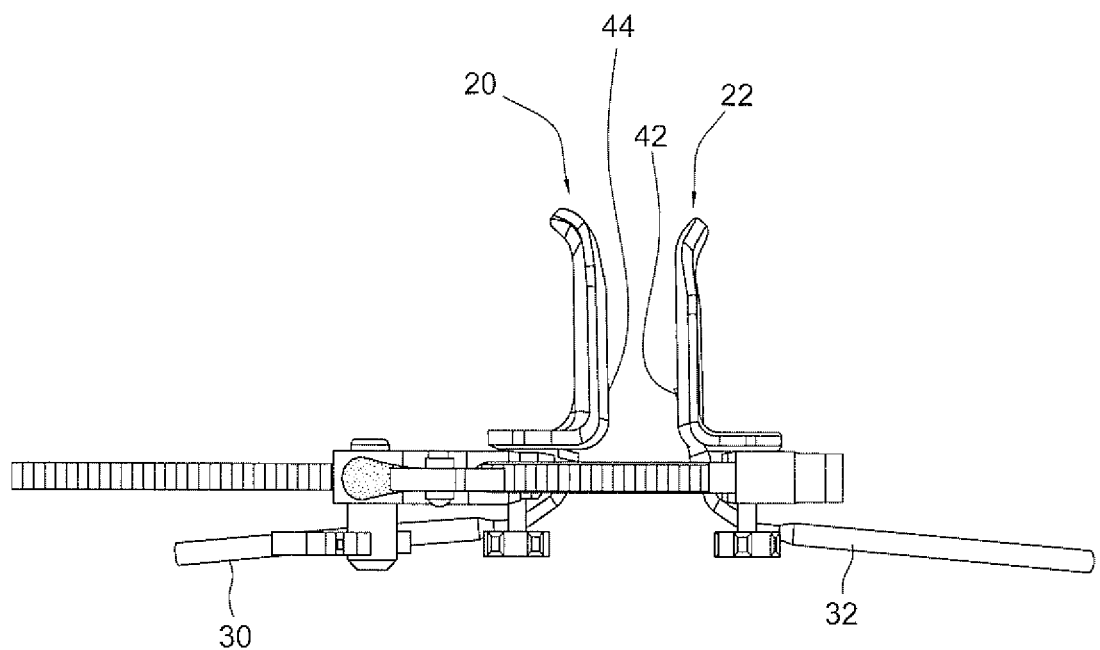
FIG. 4 is a top view of the surgical retractor.
Figure 5:
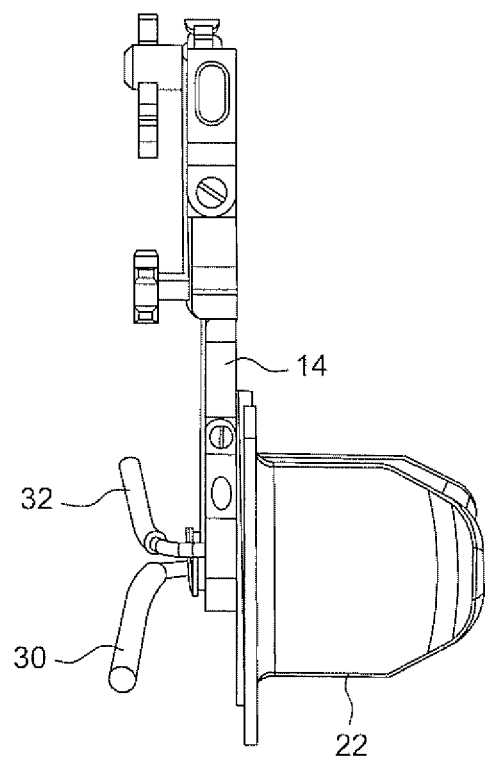
FIG. 5 is an end view of the surgical retractor.
Figure 6:
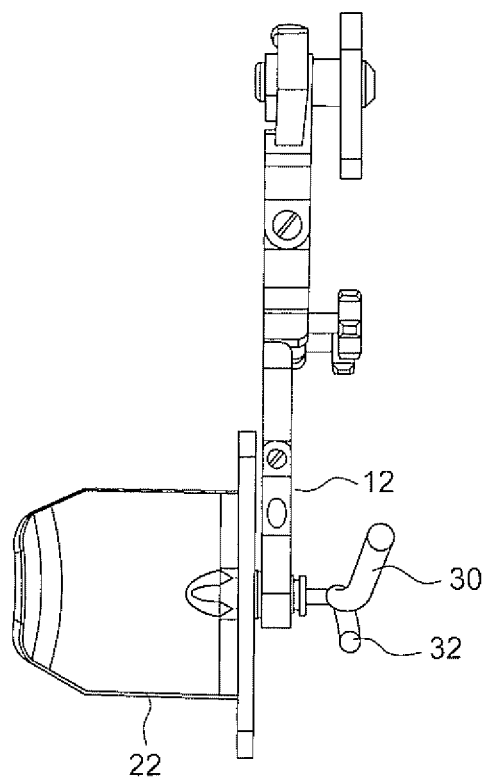
FIG. 6 is an end view of the surgical retractor taken from the other end.
Figure 7:
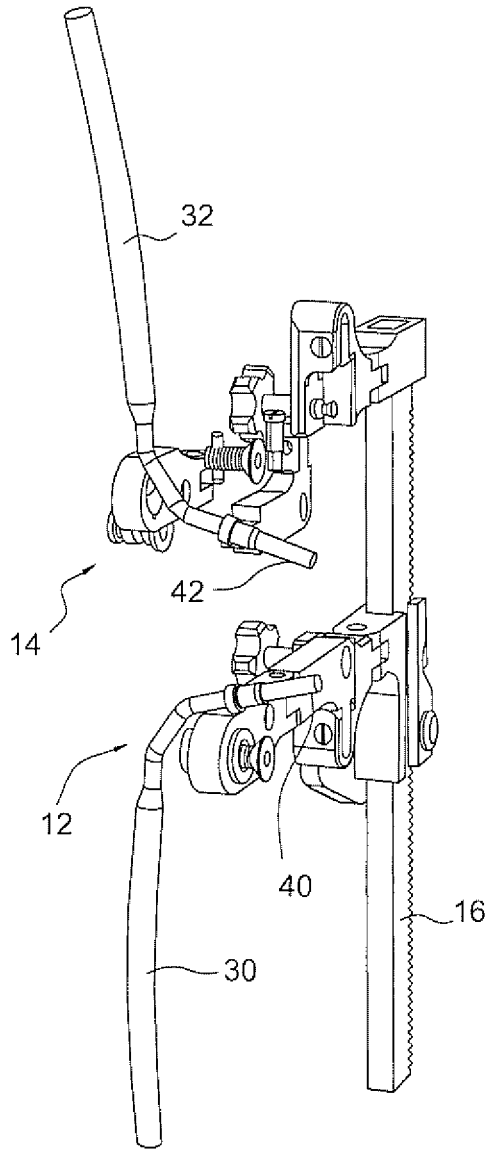
FIG. 7 is part of an explosive view of the surgical retractor showing the blades removed.

Some preferred embodiments of a surgical retractor and method will now be described with reference to the drawing figures, in which like reference numbers refer to like parts.

A preferred embodiment of a retractor is shown in FIGS. 1-6. The retractor 10 generally includes a first arm assembly 12 and a second arm assembly 14. The arm assembly 14 also includes a rack 16, and the arm assembly 12 is slideable along the rack 16 to move the arms 12 and 14 towards or away from each other and lock them in a desired position. The arm 12 supports a blade 20, and the arm 14 supports a blade 22. The blade 20 has an intermediate portion 24 which has a curvature which may be referred to as a concave curvature as it faces towards to blade 22. The blade 22 has an intermediate portion 26 which may be referred to as having a convex curvature as it faces towards the blade 20. The blade 20 is pivotally mounted to the arm 12 by a blade pivot 21. The blade 22 is pivotally mounted to the arm 14 by a blade pivot 23. Attached to the blade 20 is a fiber optic or other light source 30 and similarly attached to the blade 22 is a fiber optic or other light source 32. The fiber optic light source 30 penetrates through the blade 20 and projects through an opening of the blade 20 so that it may shine towards the other blade 22 as shown. The fiber optic light source 32 has a light-emitting tip 42 that projects through the blade and projects through aperture in the blade 22 so that it may shine towards the blade 20.

The retractor 10 holds an incision between the ribs open during surgery. In particular, the blades 20 and 22 are adapted to reduce pressure and trauma to the ribs and surrounding tissue and nerves, by being designed to anatomically fit the shape of the ribs and avoid pressure points. This is accomplished at least in part by the shape of the blades, where the blades 20 and 22 each have a convex or concave curvature in the same direction as each other. That is, one blade has a convex profile, and looking in the reverse direction, the other blade faces the first blade in a concave direction. The surfaces of the blade having these relative convex and concave profiles, are the outer surfaces of a blade (i.e., the surfaces of the blade facing away from each other). The curved profiles may be implemented on a portion of the blades in the illustrated example, the blades have a substantially constant thickness in these intermediate convex/concave portions, and therefore their inner surfaces (facing towards each other) also feature complimentary convex and concave surfaces. However, this is not necessary and the convex/concave relationship being recited may be only in the outward facing surfaces, which are the surfaces that control the ribs or other anatomy.

The blades are preferably designed in some embodiments so that the convex or concave curve of the outer blade surfaces matches the general placement of the lower and upper surface of the ribs being contacted. If the inner surfaces (those facing each other) of the respective blades also have a complimentary matching surface curvature (that is if each blade has a substantially constant thickness in this intermediate region), another benefit can be achieved whereby the viewing area into the surgical area is maximized.

The illustrated lighting devices 30 and 32 having light-projecting terminals 40 and 42, respectively, which are optional but can provide illumination into the area of surgery. In illustrated embodiment, the lighting devices 30 and 32 are attached to the blade and pass through part of the blade terminating at a small aperture in the blade provided to permit the transmission of light.

Figure 8:
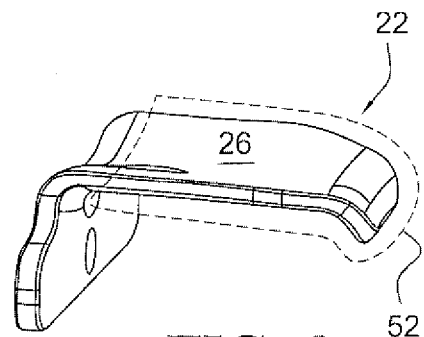
FIG. 8 is an exploded detailed view of a single blade, showing an embodiment with silicon cushioning.
Figure 9:
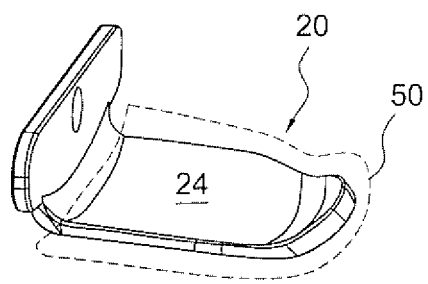
FIG. 9 is an exploded view of a second blade showing an embodiment having silicon cushioning on the blade.

FIGS. 8 and 9 show an additional embodiment of the invention. In this embodiment, an elastic cushioning material or sleeve 50 and 52 is provided on the blades 20 and 22, respectively. The elastic cushioning may preferably be a soft silicone material, or another soft elastic material. The material may be over-molded on top of part or all of the blade themselves during or after manufacturing. Alternatively or in addition, the cushioning may be a removable, semi-permanent, or permanent, sleeve shaped to cover all or part of the blades. In some embodiments, the cushioning will cover a part of the blade 50 or 52, for example some or all of the curved intermediate portions 24 and 26.

Some details of the pivoting arms 12 and 14 to which the blades 20 and 22 are mounted, can be found in U.S. Pat. No. 7,537,565, the disclosure of which is incorporated herein in its entirely by reference. U.S. Pat. No. 7,537,565 discloses among other things pivoting arms which can support retractor blades. The fiber optic light source 30 has a light-emitting tip 40 that projects through the blade and projects through aperture in the blade 20 so that it may shine towards the blade 22.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A surgical retractor, comprising:
a pair of arms mounted to be laterally slideable towards and apart from each other;
a first retractor blade having a first height dimension in the proximal-distal direction and a first width dimension transverse the first height dimension, the first retractor blade comprising a first proximal top portion, a first intermediate portion, and a first distal end portion; and
a second retractor blade having a second height dimension in the proximal-distal direction and a second width dimension transverse the second height dimension, the second retractor blade comprising a second proximal top portion, a second intermediate portion, and a second distal end portion,
wherein a first arm of the pair of arms engages the first proximal top portion of the first retractor blade and a second arm of the pair of arms engages the second proximal top portion of the second retractor blade,
wherein the first intermediate portion of the first retractor blade comprises an inner surface and first outer surface that faces away from the second retractor blade and the second intermediate portion of the second retractor blade comprises inner surface and a second outer surface that faces away from the first retractor blade,
wherein the first outer surface is convex along the first width dimension and the second outer surface is concave along the second width dimension, and
wherein the first distal end portion flares outward away from the second retractor blade along the first height dimension and the second distal end portion flares outward away from the first retractor blade along the second height dimension, wherein the first and second arms each have longitudinal axes and when the blades are positioned between the axes, the curved shape of the blades are complimentary and capable of mating.

2. The retractor of claim 1, wherein the first retractor blade and the second retractor blade each comprise a cushioned material on the blade where the blade contacts the anatomy.

3. The retractor of claim 2, wherein the cushioned material is made of a soft silicone.

4. The retractor of claim 2, wherein the cushioned material is affixed to the first retractor blade and the second retractor blade.

5. The retractor of claim 1, further comprising a light source mounted to a lit blade comprising one of the first retractor blade and the second retractor blade.

6. The retractor of claim 5, wherein the light source comprises a fiber optic light source that penetrates into and through the lit blade and terminates in an opening in the lit blade facing inward whereby light shines inwardly towards another blade other than the lit blade and comprising one of the first retractor blade and the second retractor blade.

7. The retractor of claim 5, wherein the other blade comprises another light source mounted thereto.

8. A surgical retractor, comprising:
a first arm having a longitudinal axis;
a first retractor blade connected to the first arm, the first retractor blade having a first outer surface with a convex shape;
a second arm having a longitudinal axis; and
a second retractor blade connected to the second arm, the second retractor blade having a second outer surface with a concave shape, wherein the first and second arms are mounted to be laterally slideable towards and apart from each other, and so that a first inner surface of the first retractor blade opposite the first outer surface and a second inner surface of the second retractor blade opposite the second outer surface face towards each other wherein a first distal end portion on the first blade flares outward away from the second retractor blade along the first height dimension and a second distal end portion on the second blade flares outward away from the first retractor blade along the second height dimension, wherein when the blades are positioned between the respective longitudinal axes of the first arm and second arm, the curved shape of the blades are complimentary and capable of mating.

9. The retractor of claim 8, wherein the first retractor blade and the second retractor blade each comprise a cushioned material on the respective retractor blade at a portion where the respective blade contacts the respective rib surface.

10. The retractor of claim 9, wherein the cushioned material is made of a soft silicone.

11. The retractor of claim 9, wherein the cushioned material is affixed to the first retractor blade and the second retractor blade.

12. The retractor of claim 8, further comprising a light source mounted to a lit blade comprising one of the first retractor blade and the second retractor blade.

13. The retractor of claim 12, wherein the light source comprises a fiber optic light source that penetrates into and through the lit blade and terminates in an opening in the lit blade facing inward whereby light shines inwardly towards another blade other than the lit blade and comprising one of the first retractor blade and the second retractor blade.

14. The retractor of claim 12, wherein the other blade comprises another light source mounted thereto.

15. The retractor of claim 8, wherein the first retractor blade has a first inner surface that is convex, and the second retractor blade has a second inner surface that is concave.

16. A surgical retractor, comprising:
a first retractor blade connected to a first arm having a longitudinal axis, the first retractor blade having a first outer surface that is convexly contoured in a direction transverse to a longitudinal axis thereof and is concavely contoured along a portion of the longitudinal axis, the first retractor blade further having an inner surface;
a second retractor blade connected to a second arm having a longitudinal axis, the second retractor blade having a second outer surface that is concavely contoured in a direction transverse to the longitudinal axis and is concavely contoured along a portion of the longitudinal axis, the second retractor blade further having an inner surface; and
a mount having a first arm and a second arm to which the first and second retractor blades are mounted to be laterally slideable towards and apart from each other, and so that the first outer surface and the second outer surface face away from each other such that when the blades are positioned between the respective longitudinal axes, the contoured shape of the inner surfaces of the respective blades are complimentary and capable of mating.

17. The retractor of claim 16, wherein the mount comprises a first arm and a second arm.

18. The retractor of claim 17, wherein the first arm comprises a rack slidably engageable with the second arm.

19. The retractor of claim 17, wherein the first retractor blade is pivotally mounted to the first arm, and the second retractor blade is pivotally mounted to the second arm.

* * * * *